(12) United States Patent
Forsell

(10) Patent No.: US 6,453,907 B1
(45) Date of Patent: *Sep. 24, 2002

(54) FOOD INTAKE RESTRICTION WITH ENERGY TRANSFER DEVICE

(75) Inventor: Peter Forsell, Menzingen (CH)

(73) Assignee: Obtech Medical AG, Baar (CH)

( * ) Notice: Subject to any disclaimer, the term of this patent is extended or adjusted under 35 U.S.C. 154(b) by 0 days.

This patent is subject to a terminal disclaimer.

(21) Appl. No.: 09/502,486

(22) Filed: Feb. 11, 2000

Related U.S. Application Data

(60) Provisional application No. 60/148,345, filed on Aug. 12, 1999.

(51) Int. Cl.[7] .................................................. A61F 2/00
(52) U.S. Cl. ........................................ 128/899; 600/37
(58) Field of Search ................................. 128/897–899; 600/29–32, 37, 593; 606/139–141, 151, 157, 201–203, 213, 218; 607/41

(56) References Cited

U.S. PATENT DOCUMENTS

| | | | | |
|---|---|---|---|---|
| 3,750,194 A | * | 8/1973 | Summers .................. 600/31 X |
| 3,875,928 A | * | 4/1975 | Angelchik ................... 600/37 |
| 4,246,893 A | * | 1/1981 | Berson ...................... 128/898 |
| 4,592,355 A | * | 6/1986 | Antebi ....................... 606/144 |
| 4,696,288 A | * | 9/1987 | Kuzmak et al. ............. 128/898 |
| 5,074,868 A | * | 12/1991 | Kuzmak ..................... 606/157 |
| 5,160,338 A | * | 11/1992 | Vincent ..................... 606/157 |
| 5,226,429 A | * | 7/1993 | Kuzmak ..................... 128/898 |
| 5,449,368 A | * | 9/1995 | Kuzmak ..................... 606/157 |
| 5,509,888 A | * | 4/1996 | Miller ......................... 600/29 |
| 5,704,893 A | * | 1/1998 | Timm ......................... 600/29 |
| 5,769,877 A | * | 6/1998 | Barreras ..................... 607/61 |
| 5,771,903 A | | 6/1998 | Jakobsson |
| 5,910,149 A | * | 6/1999 | Kuzmak ..................... 606/157 |
| 5,938,669 A | * | 8/1999 | Klaiber et al. .............. 606/157 |
| 5,978,712 A | * | 11/1999 | Suda et al. ................. 607/41 |
| 6,074,341 A | * | 6/2000 | Anderson et al. ............ 600/29 |

FOREIGN PATENT DOCUMENTS

| | | |
|---|---|---|
| FR | 2692777 | 12/1993 |
| WO | WO 00/09048 | 2/2000 |
| WO | WO 00/15158 A1 | 3/2000 |

\* cited by examiner

*Primary Examiner*—Kevin Shaver
*Assistant Examiner*—Joseph A. Cadugan
(74) *Attorney, Agent, or Firm*—Nixon & Vanderhye, P.C.

(57) ABSTRACT

A food intake restriction apparatus and method for an obese patient includes and uses an energy transmission device for wireless transmission of energy of a first form from outside the patient's body. An operable restriction device is implanted in the patient and engages the stomach or the esophagus to form an upper small pouch of the stomach, and a restricted stoma opening is formed in the stomach or esophagus. The restriction device is operable in response to a second energy form different than the first form to vary the restricted stoma. An energy transfer device is implanted in the patient for transferring energy of the first form transmitted by the energy transmission device into energy of the second form. The energy transfer device includes at least one element having a positive region and a negative region, and creating an energy field between the positive and negative regions when exposed to the first form energy transmitted by the energy transmission device, so that the energy field produces the energy of the second form.

114 Claims, 6 Drawing Sheets

FOOD INTAKE RESTRICTION WITH ENERGY TRANSFER DEVICE

CROSS REFERENCE TO RELATED APPLICATION

This application is based upon provisional application Ser. No. 60/148,345 filed Aug. 12, 1999, the disclosure of which is hereby incorporated by reference herein.

BACKGROUND OF THE INVENTION

The present invention relates to a food intake restriction apparatus and method. More specifically, the invention relates to a food intake restriction apparatus and method for surgical application in the abdomen of a patient for forming a restricted stoma opening in the stomach or esophagus. The term "patient" includes an animal or a human being.

Food intake restriction apparatus in the form of a gastric banding device, in which a band encircles a portion of a patient's stomach to restrict the food intake of the patient, have been used in surgery for morbid obesity to form a small gastric pouch above the band and a reduced stoma opening in the stomach. Although such a band is applied around the stomach to obtain an optimal stoma opening during surgery, some prior gastric banding devices are provided with an adjustment means enabling a minor post-operation adjustment of the size of the stoma opening. In all such prior art devices such as disclosed in U.S. Pat. No. 4,592,339, European Pat. No. 0611561 and International Patent Application WO 94/27504, the adjustment means typically comprises an inflatable cavity in the band and an injection port in fluid connection with the inflatable cavity for adding fluid to or withdrawing fluid from the latter. In practice, the band is made of silicone rubber which is a material approved for implantation and the fluid is a liquid such as an isotonic salt solution.

It has also been found that the volume of the gastric pouch above the band increases in size up to ten times after operation. Therefore the pouch volume during surgery needs to be very small, approximately 7 ml. To enable the patient to feed the stomach with sufficient nutrition immediately after an operation considering such a small gastric pouch, the stoma initially needs to be relatively large and later needs to be substantially reduced, as the pouch volume increases. To be able to achieve a significant range of adjustment of the band, the cavity in the band has to be relatively large and is defined by a thin flexible wall, normally made of silicone material. Furthermore, the size of the stoma opening has to be gradually reduced during the first year after surgery as the gastric pouch increases in size. As indicated above, the reduction of the stoma opening using the prior art devices is achieved by adding liquid to the cavity of the band via the injection port to expand the band radially inwardly.

A great disadvantage of repeatedly injecting liquid via the injection port is the increased risk of the patient getting an infection in the body area surrounding the injection port. If such an infection occurs the injection port has to be surgically removed from the patient. Moreover, such an infection might be spread along the tube interconnecting the injection port and the band to the stomach, causing even more serious complications. Thus, the stomach might be infected where it is in contact with the band, which might result in the band migrating through the wall of the stomach. Also, it is uncomfortable for the patient when the necessary, often many, post-operation adjustments of the stoma opening are carried out using an injection needle penetrating the skin of the patient into the injection port.

It may happen that the patient swallows pieces of food too large to pass through the restricted stoma opening. If that occurs the patient has to visit a doctor who can remove the food pieces, if the band design so permits, by withdrawing some liquid from the band to enlarge the stoma opening to allow the food pieces to pass the stoma. Then, the doctor has to add liquid to the band in order to regain the restricted stoma opening. Again, these measures require the use of an injection needle penetrating the skin of the patient, which is uncomfortable for the patient.

SUMMARY OF THE INVENTION

The object of the present invention is to provide a new convenient food intake restriction apparatus for forming a stoma opening in the stomach or esophagus of a patient which is easy to adjust and does not require the use of an injection needle for accomplishing post-operation adjustments of the stoma opening.

According to one aspect of the present invention a food intake restriction apparatus is provided which comprises: An energy transmission device for wireless transmission of energy of a first form from outside a patient's body. An operable restriction device implanted in the patient and engaging the stomach or esophagus to form a restricted stoma opening in the stomach or esophagus, the device operable in response to a second energy form different than the first form to vary the restricted stoma opening. And, an energy transfer device implanted in the patient for transferring energy of the first form transmitted by the energy transmission device into energy of the second form, the energy transfer device comprising at least one element having a positive region and a negative region, and creating an energy field between the positive and negative regions when exposed to the first form energy transmitted by the energy transmission device, so that the energy field produces the energy of the second form.

As a result, the advantage is achieved that the food intake restriction apparatus of the invention provides simple and effective energy transmission which ensures an extended and reliable functionality of the apparatus, possibly for the rest of the patient's natural life, and at least many years.

The restriction device preferably controls the size of the stoma opening in the stomach or esophagus, which gives the advantage that the patient can be permitted to temporarily increase the size of the stoma opening in case pieces of food get stuck in the stoma opening. It would be very difficult for the patient to remove a stuck food piece if the patient were unable to enlarge the size of the stoma opening.

Advantageously, the restriction device is directly operated with the energy of the second form, preferably in a non-magnetic and/or non-mechanical manner, as the energy transmission device transmits the energy of a first form. The restriction device may be directly operated with the energy of the second form without externally touching subcutaneously implanted components of the apparatus. The advantage of directly using energy as it is transmitted is that the apparatus can be of a very simple design and the few components involved makes the apparatus extremely reliable.

The restriction device may be non-inflatable, i.e. with no hydraulic or pneumatic fluid involved for the adjustments of the restriction device. This eliminates problems with fluid leaking from the restriction device.

In accordance with a preferred embodiment of the invention, the element comprises an electrical junction element, and the electrical junction element is capable of inducing an electric field between the positive and negative regions when exposed to the energy of a first form transmitted by the energy transmission device, whereby the energy of a second form comprises electric energy.

Consequently, the restriction device suitably is electrically operated, whereby the positive and negative regions of the electrical junction element supply electric energy for the operation of the restriction device. The apparatus suitably comprises implanted electric conductors connected to the positive and negative regions of the electrical junction element, whereby the electrical junction element is capable of supplying an electric current, such as a direct current, a pulsating direct current, a combination of a direct and pulsating direct current, an alternating current or a combination of a direct and alternating current, via the conductors. Furthermore, the electrical junction element may be capable of supplying a frequency, amplitude, or frequency and amplitude modulated analog, digital, or a combination of analog and digital signal, which is used in connection with control of the restriction device.

The element, preferably in the form of an electrical semiconductor junction element, suitably forms a flat and thin sheet and has a volume of less than 2000 $cm^3$ to be suited for subcutaneous implantation, so that the electrical junction element is located just behind the skin of the patient. The electrical junction element should be designed to generate an output current exceeding 1 $\mu A$ when exposed to the energy of the first form transmitted by the energy transmission device. Of course, all the components of the energy transfer device including the electrical junction element in contact with the patient's body should be of a biocompatible material. Alternatively, it would be possible to implant the energy transfer device in the thorax or cephal region of the patient, or in an orifice of the patient's body and under the mucosa or intraluminar outside the mucosa of the orifice.

For in vitro appliances, a particular type of an electrical semiconductor junction element has been commonly used, namely a so called p-n (positive/negative) junction element, typically in the form of solar cells. A solar cell transfers solar energy in the form of visible light into electric energy in the form of direct current. For example, a p-n junction element may comprise two layers of semiconductor, one p-type (positive) and the other n-type (negative), sandwiched together to form a "p-n junction". This p-n junction induces an electric field across the element when absorbing quanta of light (photons).

To be more precise, the quanta of light transfer their energy to some of the semiconductor's electrons, which are then able to move about through the material. For each such negatively charged electron, a corresponding positive charge—a "hole"—is created. In an ordinary semiconductor, these electrons and holes recombine after a short time and their energy is wasted as heat. However, when the electrons and holes are swept across the p-n junction in opposite directions by the action of the electric field, the separation of charge induces a voltage across the p-n junction element. By connecting the p-n junction element to an external circuit, the electrons are able to flow thereby creating a current.

Surprisingly, it has been proven that although both the skin and subcutis absorb energy from an external light beam directed against the skin portion behind which a properly designed p-n junction element is located, the light energy transmitted through the skin can induce a current from the p-n junction element strong enough (minimum 1 $\mu A$) to enable the operation of the electrically operated restriction device. Thus, such a p-n junction element is now for the first time used for in vivo applications.

However, the apparatus of the present invention is not limited to the use of visible light for the wireless transmission of energy. Thus, in accordance with a broad aspect of the invention, the energy transmission device transmits energy by at least one wireless signal, preferably containing radiant energy.

The wireless signal may comprises a wave signal, for example an electromagnetic wave signal, such as an infrared light signal, a visible light signal, an ultra violet light signal, a laser signal, a micro wave signal, a radio wave signal, an x-ray radiation signal, and a gamma radiation signal. Where applicable, one or more of the above signals may be combined. Alternatively, the wave signal may comprise a sound wave signal, such as an ultrasonic signal. Generally, the wireless signal may comprise a digital, analog or a digital and analog signal.

The energy of the first form transmitted by the energy transmission device may comprise an electric or magnetic field transmitted in pulses, for example digital pulses. Furthermore, the energy transfer device may transfer the energy of the first form, which may comprise polarized energy, into a direct current, pulsating direct current, a combination of a direct and pulsating direct current, an alternating current or a combination of a direct and alternating current. Alternatively, the energy of the first form may comprise kinetic energy.

The energy of the second form may comprise a frequency, amplitude or frequency and amplitude modulated analog, digital or combined analog and digital signal.

The apparatus may further comprise an implanted pulse generator for generating electrical pulses from the energy of the second form rendered by the energy field created by the element having positive and negative regions.

In accordance with another embodiment of the invention, the apparatus comprises an implanted operation device for operating the restriction device and a control device for controlling the operation device, wherein the element powers the operation device with the energy of the second form. The operation device preferably comprises a motor, for example an electric linear motor or an electric rotary motor which is controlled by the control device to rotate a desired number of revolutions. The electric motor may have electrically conductive parts made of plastics. Alternatively, the motor may comprise a hydraulic or pneumatic fluid motor, wherein the control device controls the fluid flow through the fluid motor. Motors currently available on the market are getting smaller and smaller. Furthermore, there is a great variety of control methods and miniaturized control equipment available. For example, a number of revolutions of a rotary motor may be analyzed by a Hall-element just a few mm in size.

In accordance with another embodiment of the invention, the restriction device comprises hydraulic means and the operation device comprises a pump for pumping a fluid in the hydraulic means, a motor for driving the pump, a valveless fluid conduit between the pump and the hydraulic means of the restriction device, and a reservoir for fluid, wherein the reservoir forms part of the conduit. All of the hydraulic components involved are preferably devoid of any non-return valve. This is of great advantage, because with valves involved there is always a risk of malfunction due to improperly working valves, especially when long time periods passes between valve operations. The reservoir may form a fluid chamber with a variable volume, and the pump may distribute fluid from the chamber to the hydraulic means of the restriction device by reduction of the volume of the chamber and withdraws fluid from the hydraulic means to the chamber by expansion of the volume of the chamber.

The control device may reverse the operation device by shifting polarity of the energy of the second form. Where the operation device comprises an electric motor the energy of the second form suitably comprises electric energy.

In accordance with yet another embodiment of the invention, the restriction device is operable to perform a reversible function, such as enlarging and restricting the food passageway, and there is a reversing device implanted in the patient for reversing the function performed by the restriction device. Such a reversing function preferably involves enlarging and restricting the stoma opening by the restriction device, suitably in a stepless manner. In this connection, the control device suitably controls the reversing device, which may include a switch, to reverse the function performed by the restriction device. The reversing device may comprise hydraulic means including a valve for shifting the flow direction of a fluid in the hydraulic means. Alternatively, the reversing device may comprise a mechanical reversing device, such as a switch or a gear box.

Where the reversing device comprises a switch the control device suitably controls the operation of the switch by shifting polarity of energy supplied to the switch. The switch may comprise an electric switch and the source of energy may supply electric energy for the operation of the switch.

In accordance with a advantageous embodiment of the invention, the apparatus further comprises an energy storage device implanted in the patient for storing the energy of the second form and for supplying energy in connection with the operation of the restriction device. The implanted energy storage device preferably comprises an electric source of energy, such as an accumulator, a rechargeable battery or a combination of an accumulator and rechargeable battery.

The apparatus may further comprise a switch implanted in the patient for switching the operation of the restriction device and a source of energy implanted in the patient. This embodiment is particularly suited for applications where the energy transmission efficiency of the apparatus is insufficient, i.e. where the implanted restriction device is to perform more advanced operations. Such a source of energy preferably is a battery. Alternatively, the source of energy is an accumulator which also may store the energy of the second form.

In accordance with a first alternative, the switch is operated by the energy of the second form supplied by the energy storage device to switch from an off mode, in which the source of energy is not in use, to an on mode, in which the source of energy supplies energy for the operation of the restriction device. In this case, the implanted source of energy may comprise a battery, preferably having a life-time of at least 10 years, or an accumulator. However, other kinds of sources are also conceivable, such as a nuclear source of energy or a chemical source of energy.

In accordance with a second alternative, the apparatus further comprises a remote control for controlling the supply of energy of the implanted source of energy, wherein the switch is operated by the energy of the second form supplied by the energy storage device to switch from an off mode, in which the remote control is prevented from controlling the source of energy and the source of energy is not in use, to a standby mode, in which the remote control is permitted to control the source of energy to supply energy for the operation of the restriction device.

In accordance with a third alternative, the energy storage device is omitted, wherein the switch is operated by the energy of the second form supplied by the energy transfer device to switch from an off mode, in which the remote control is prevented from controlling the source of energy and the source of energy is not in use, to a standby mode, in which the remote control is permitted to control the source of energy to supply energy for the operation of the restriction device.

In accordance with a fourth alternative, also the remote control is omitted, wherein the switch is operated by the energy of the second form supplied by the energy transfer device to switch from an off mode, in which the source of energy is not in use, to an on mode, in which the source of energy supplies energy for the operation of the restriction device. Where applicable, in the described embodiments the switch may switch when the energy transmission device is transmitting wireless energy, preferably while the transferred energy of the second form is stabilized by an implanted capacitor, which may temporarily (for a few seconds) store the energy of the second form.

The switch mentioned above may comprise an electronic switch or, where applicable, a mechanical switch.

The advantage of using a switch above all is increased control safety, i.e. interfering signals in the patient's surroundings cannot affect the implanted restriction device. Furthermore, the lifetime of the implanted source of energy will be significantly prolonged, since the energy consumption of the apparatus will be reduced to a minimum. During the above mentioned standby mode, the remote control uses energy from the implanted source of energy. By means of the energy transmission device energy may be transmitted to activate the switch to connect the implanted source of energy only when energy is required in connection with the operation of the restriction device.

All of the above embodiments may be combined with at least one implanted sensor for sensing at least one physical parameter of the patient, wherein the control device may control the restriction device in response to signals by the sensor. For example, the sensor may comprise a pressure sensor for directly or indirectly sensing the pressure against the restriction device, human tissue or in the stomach or esophagus. The pressure sensor may be any suitable known or conventional pressure sensor such as shown in U.S. Pat. Nos. 5,540,731, 4,846,181, 4,738,267, 4,571,749, 4,407,296 or 3,939,823; or an NPC-102 Medical Angioplasty Sensor. The control device may comprise an internal control unit implanted in the patient for, preferably directly, controlling the restriction device in response to signals from the sensor. In response to signals from the sensor, for example pressure, the patient's position or any other important physical parameter, the internal control unit may send information thereon to outside the patient's body. The control unit may also automatically control the restriction device in response to signals from the sensor. For example, the control unit may control the restriction device to further restrict the food passageway in the stomach in response to the sensor sensing that the patient is lying, or enlarge the food passageway in response to the sensor sensing an abnormally high pressure against the restriction device.

Alternatively, the control device may comprise an external control unit outside the patient's body for, suitably directly, controlling the restriction device in response to signals by the sensor. The external control unit may store information on the physical parameter sensed by the sensor and may be manually operated to control the restriction device based on the stored information. In addition, there may be at least one implanted sender for sending information on the physical parameter sensed by the sensor.

An external data communicator may be provided outside the patient's body and an internal data communicator may be implanted in the patient for communicating with the external communicator. The implanted communicator may feed data related to the patient, or related to the implanted restriction device, back to the external communicator. Alternatively or in combination, the external communicator may feed data to the internal communicator. The implanted communicator may suitably feed data related to at least one physical signal of the patient. The arrangement of external and internal communicators gives the advantage, among other things, that a long term control of activities related to the implanted restriction device.

The apparatus may further comprise an implanted programmable control unit for controlling the restriction device, preferably over time in accordance with an activity schedule program. This will advance the apparatus and make possible an adaptation of the apparatus to the individual patients.

All of the above embodiments are preferably remote controlled. Thus, the apparatus advantageously comprises a wireless remote control transmitting at least one wireless control signal for controlling the restriction device. With such a remote control it will be possible for a doctor to readily adapt the function of the apparatus to the patient's need, which is beneficial with respect to the treatment of the patient in the long run.

The wireless remote control may be capable of obtaining information on the condition of the implanted restriction device and of controlling the restriction device in response to the information. Also, The remote control may be capable of sending information related to the restriction device from inside the patient's body to the outside thereof.

In a particular embodiment of the invention, the wireless remote control comprises at least one external signal transmitter or transceiver and at least one internal signal receiver or transceiver implanted in the patient. In another particular embodiment of the invention, the wireless remote control comprises at least one external signal receiver or transceiver and at least one internal signal transmitter or transceiver implanted in the patient.

The wireless remote control may transmit a carrier signal for carrying the control signal, wherein the carrier signal is frequency, amplitude or frequency and amplitude modulated and is digital, analog or digital and analog. Also the control signal used with the carrier signal may be frequency, amplitude or frequency and amplitude modulated.

The control signal may comprise a wave signal, for example, a sound wave signal, such as an ultrasound wave signal, an electromagnetic wave signal, such as an infrared light signal, a visible light signal, an ultra violet light signal, a laser signal, a micro wave signal, a radio wave signal, an x-ray radiation signal, or a gamma radiation signal. Where applicable, two or more of the above signals may be combined.

The control signal may be digital or analog, and may comprise an electric or magnetic field. Suitably, the wireless remote control may transmit an electromagnetic carrier wave signal for carrying the digital or analog control signal. For example, use of an analog carrier wave signal carrying a digital control signal would give safe communication. The control signal may be transmitted in pulses by the wireless remote control.

Alternatively, in the above embodiments a semiconductor circuitry, a transistor circuitry or a microchip may be substituted for the element of the apparatus having positive and negative regions.

The energy transfer device of the apparatus may be implanted, for example subcutaneously, in the abdomen, thorax or cephal region, or other locations in the patient's body.

In accordance with another aspect of the invention, there is provided an implanting method, comprising the steps of providing a food intake restriction apparatus as described above, cutting an opening in a patient's mucosa in an orifice of the patient's body, and implanting the energy transfer device in the patient's body through the opening. Alternatively, the cutting step may comprise cutting an opening in the patient's skin and the implanting step may comprise implanting the energy transfer device in the patient's body through the opening.

In accordance with yet another aspect of the invention, there is provided a laparoscopic surgical method of implanting a food intake restriction apparatus, comprising: a) Placing at least two laparoscopic trocars within the patient's body. c) Using at least one dissecting tool inserted through the laparoscopic trocars, dissecting the region of the esophagus or stomach. d) Introducing the restriction device through the trocars. e) Placing a restriction device of the apparatus in the dissected area in engagement with the esophagus or stomach to create a restricted stoma. And f) implanting an energy transfer device of the apparatus for transferring wireless energy into energy of a form suited for operating the restriction device. The method may further comprise postoperatively adjusting the restricted stoma in a non-invasive procedure, e.g. at least once during the first year after the surgical procedure, and typically a plurality of times in the first year.

It is the primary object of the present invention to provide a simple yet effective method and apparatus for morbid obesity in humans or animals. This and other objects of the invention will become clear from an inspection of the detailed description of the invention and from the appended claims.

BRIEF DESCRIPTION OF THE DRAWINGS

Referring to the drawing figures, like reference numerals designate identical or corresponding elements throughout the several figures.

DETAILED DESCRIPTION OF THE DRAWINGS

Figure 1:
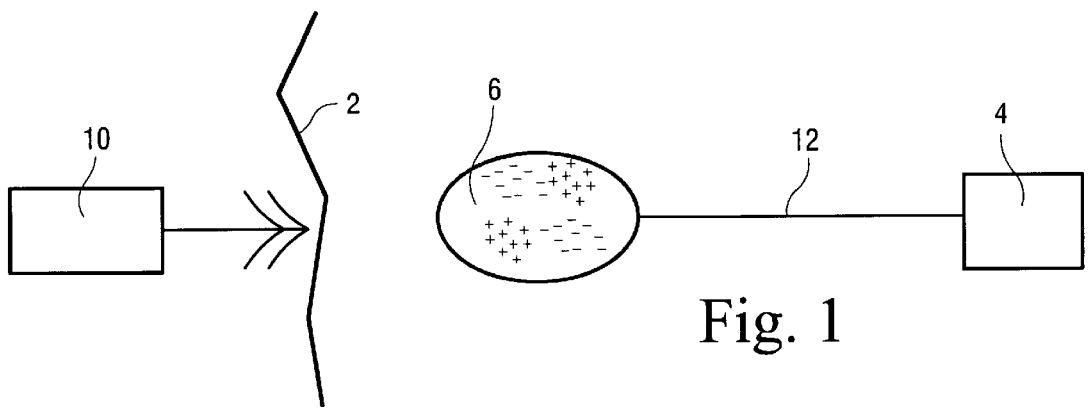
FIGS. 1 to 12 are schematic block diagrams illustrating twelve embodiments, respectively, of the food intake restriction apparatus of the invention, in which wireless energy is transmitted from outside a patient's body to energy consuming components of the apparatus implanted in the patient.

FIG. 1 schematically shows a very simple embodiment of the food intake restriction apparatus of the invention having some parts implanted in a patient and other parts located outside the patient's body. Thus, in FIG. 1 all parts placed to the right of the patient's skin 2 are implanted and all parts placed to the left of the skin 2 are located outside the patient's body.

The apparatus of FIG. 1 comprises an implanted operable restriction device 4, which engages the patient's stomach (or esophagus) to form an upper pouch of the stomach and a restricted stoma opening in the stomach. The restriction device 4 is capable of performing a reversible function, i.e. to enlarge and reduce the stoma opening. An implanted energy transfer device 6 is adapted to supply energy consuming components of the restriction device 4 with energy via a power supply line 12. An external energy transmission device 10 includes a wireless remote control transmitting a wireless signal which is received by a signal receiver incorporated in the implanted energy transfer device 6. The implanted energy transfer device 6 transfers energy from the signal into electric energy which is supplied via the power supply line 12 to the restriction device 4, which energy causes portions of the device 4 to move and thus adjust the stoma opening.

Figure 2:
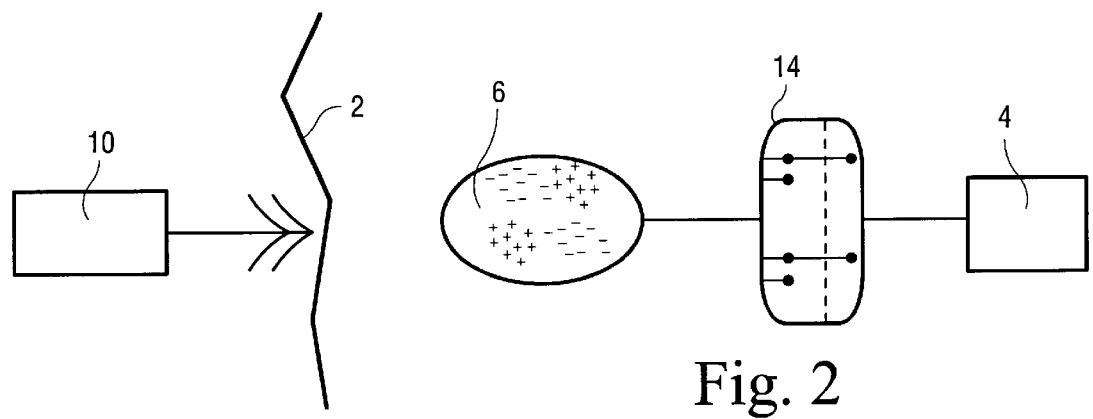

FIG. 2 shows an embodiment of the invention identical to that of FIG. 1, except that a reversing device in the form of an electric switch 14 also is implanted in the patient for reversing the restriction device 4. The wireless remote control of the external energy transmission device 10 transmits a wireless signal that carries energy and the implanted energy transfer device 6 transfers the wireless energy into a current for operating the switch 14. When the polarity of the current is shifted by the energy transfer device 6 the switch 14 reverses the function performed by the restriction device 4.

Figure 3:
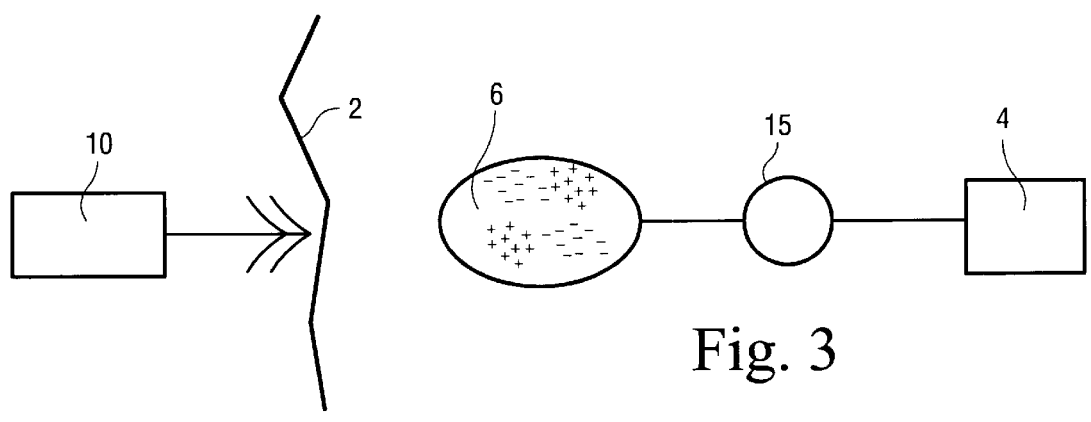

FIG. 3 shows an embodiment of the invention identical to that of FIG. 1, except that an operation device in the form of a motor 15 for operating the restriction device 4 also is implanted in the patient. The motor 15 is powered with energy from the energy transfer device 6, as the remote control of the external energy transmission device 10 transmits a wireless signal to the receiver of the energy transfer device 6.

Figure 4:
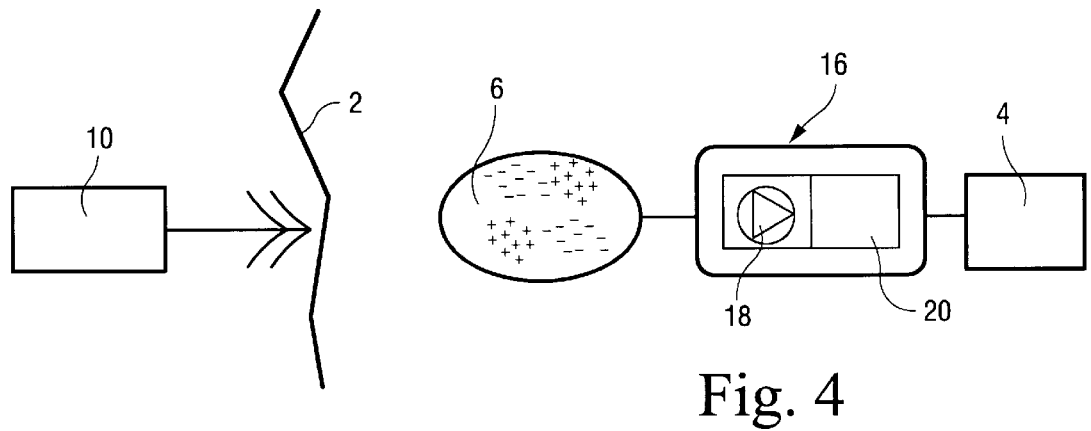

FIG. 4 shows an embodiment of the invention identical to that of FIG. 1, except that an assembly 16 including a motor/pump unit 18 and a fluid reservoir 20 also is implanted in the patient. In this case the restriction device 4 is hydraulically operated, i.e. hydraulic fluid is pumped by the motor/pump unit 18 from the reservoir 20 through a conduit 22 to the restriction device 4 to reduce the size of the stoma opening, cross-sectional area of the food passageway, and hydraulic fluid is pumped by the motor/pump unit 18 back from the restriction device 4 to the reservoir 20 to enlarge the size of the stoma opening. The implanted energy transfer device unit 6 transfers wireless energy into a current for powering the motor/pump unit 18 via an electric power supply line 24.

Figure 5:
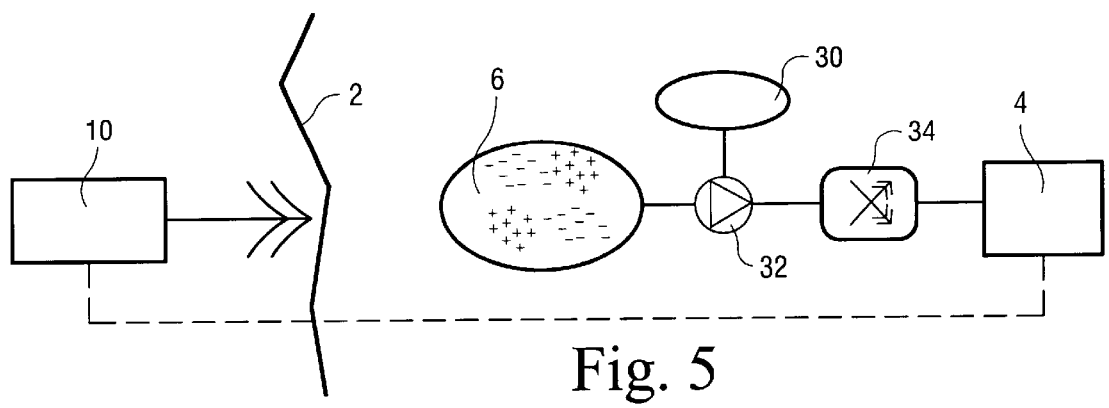

FIG. 5 shows an embodiment of the invention comprising the external energy transmission device 10 with its wireless remote control, the restriction device 4, in this case hydraulically operated, and the implanted energy transfer device 6, and further comprising an implanted hydraulic fluid reservoir 30, an implanted motor/pump unit 32 and an implanted reversing device in the form of a hydraulic valve shifting device 34. The motor of the motor/pump unit 32 is an electric motor. In response to a control signal from the wireless remote control of the external energy transmission device 10, the implanted energy transfer device 6 powers the motor/pump unit 32 with energy from the energy carried by the control signal, whereby the motor/pump unit 32 distributes hydraulic fluid between the reservoir 30 and the restriction device 4. The remote control of the energy transmission device 10 controls the shifting device 34 to shift the hydraulic fluid flow direction between one direction in which the fluid is pumped by the motor/pump unit 32 from the reservoir 30 to the restriction device 4 to reduce the size of the stoma opening, and another opposite direction in which the fluid is pumped by the motor/pump unit 32 back from the restriction device 4 to the reservoir 30 to enlarge the size of the stoma opening.

Figure 6:
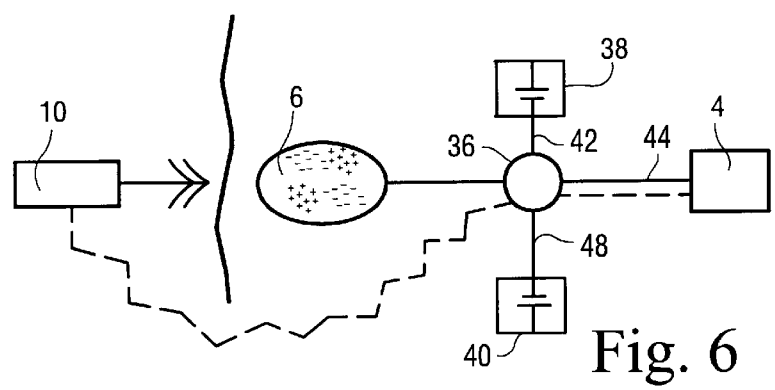

FIG. 6 shows an embodiment of the invention identical to that of FIG. 1, except that a control unit 36 controlled by the wireless remote control of the external energy transmission device 10, an accumulator 38 and a capacitor 40 also are implanted in the patient. The control unit 36 stores electric energy received from the energy transfer device 6 in the accumulator 38, which supplies energy to the restriction device 4. In response to a control signal from the wireless remote control of the energy transmission device 10, the control unit 6 either releases electric energy from the accumulator 38 and transfers the released energy via power lines 42 and 44, or directly transfers electric energy from the energy transfer device 6 via a power line 46, the capacitor 40, which stabilizes the electric current, a power line 48 and the power line 44, for the operation of the restriction device 4.

In accordance with one alternative, the capacitor 40 in the embodiment of FIG. 6 may be omitted. In accordance with another alternative, the accumulator 38 in this embodiment may be omitted.

Figure 7:
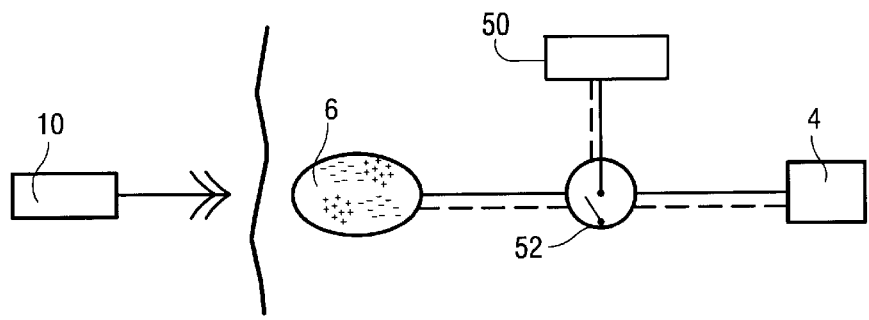

FIG. 7 shows an embodiment of the invention identical to that of FIG. 1, except that a battery 50 for supplying energy for the operation of the restriction device 4 and an electric switch 52 for switching the operation of the restriction device 4 also are implanted in the patient. The switch 52 is operated by the energy supplied by the energy transfer device 6 to switch from an off mode, in which the battery 50 is not in use, to an on mode, in which the battery 50 supplies energy for the operation of the restriction device 4.

Figure 8:
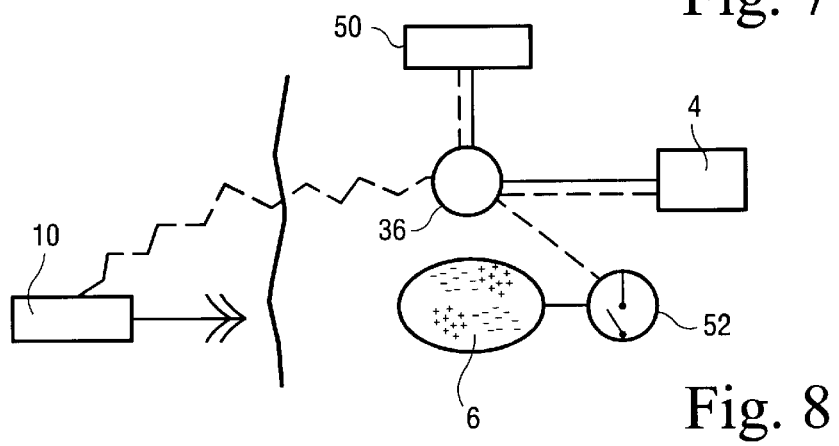

FIG. 8 shows an embodiment of the invention identical to that of FIG. 7, except that a control unit 36 controllable by the wireless remote control of the external energy transmission device 10 also is implanted in the patient. In this case, the switch 52 is operated by the energy supplied by the energy transfer device 6 to switch from an off mode, in which the wireless remote control is prevented from controlling the control unit 36 and the battery is not in use, to a standby mode, in which the remote control is permitted to control the control unit 36 to release electric energy from the battery 50 for the operation of the restriction device 4.

Figure 9:
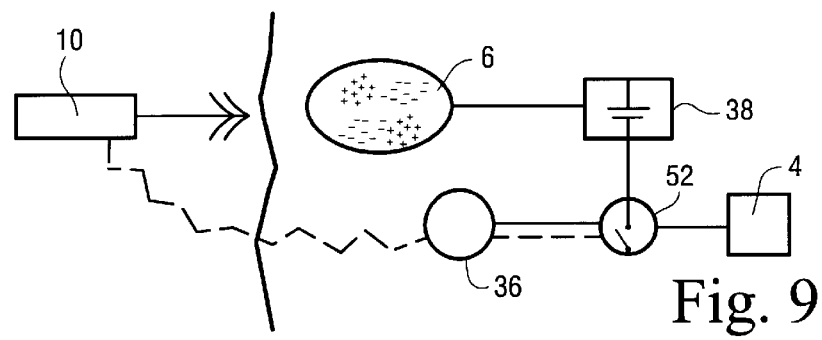

FIG. 9 shows an embodiment of the invention identical to that of FIG. 8, except that an accumulator 38 is substituted for the battery 50 and the implanted components are interconnected differently. In this case, the accumulator 38 stores energy from the energy transfer device 6. In response to a control signal from the wireless remote control of the external energy transmission device 10, the implanted control unit 36 controls the switch 52 to switch from an off mode, in which the accumulator 38 is not in use, to an on mode, in which the accumulator 38 supplies energy for the operation of the restriction device 4.

Figure 10:
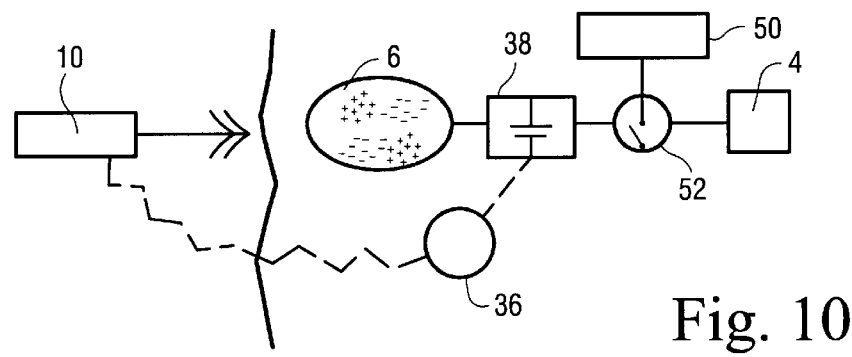

FIG. 10 shows an embodiment of the invention identical to that of FIG. 9, except that a battery 50 also is implanted in the patient and the implanted components are interconnected differently. In response to a control signal from the wireless remote control of the external energy transmission device 10, the implanted control unit 36 controls the accumulator 38 to deliver energy for operating the switch 52 to switch from an off mode, in which the battery 50 is not in use, to an on mode, in which the battery 50 supplies electric energy for the operation of the restriction device 4.

Alternatively, the switch 52 may be operated by energy supplied by the accumulator 38 to switch from an off mode, in which the wireless remote control is prevented from controlling the battery 50 to supply electric energy and is not in use, to a standby mode, in which the wireless remote control is permitted to control the battery 50 to supply electric energy for the operation of the restriction device 4.

Figure 11:
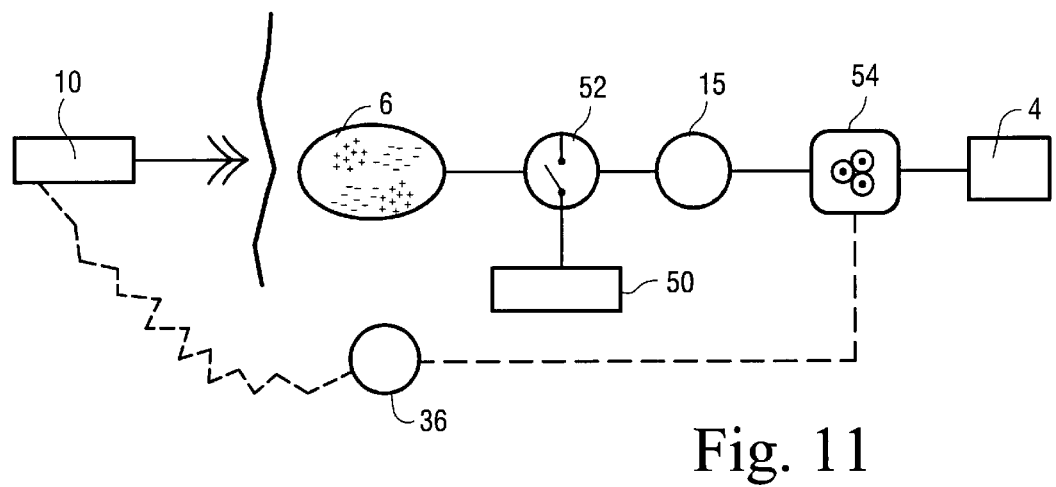

FIG. 11 shows an embodiment of the invention identical to that of FIG. 7, except that a motor 15, a mechanical reversing device in the form of a gear box 54 and a control unit 36 for controlling the gear box 54 also are implanted in the patient. The implanted control unit 36 controls the gear box 54 to reverse the function performed by the restriction device 4 (mechanically operated).

Figure 12:
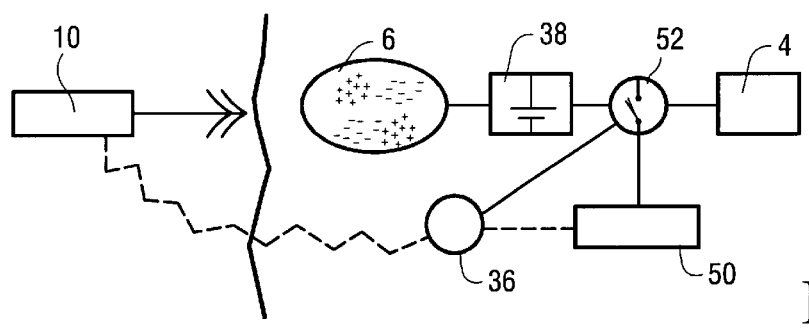

FIG. 12 shows an embodiment of the invention identical to that of FIG. 10 except that the implanted components are interconnected differently. Thus, in this case the control unit 36 is powered by the battery 50 when the accumulator 38, suitably a capacitor, activates the switch 52 to switch to an on mode. When the switch 52 is in its on mode the control unit 36 is permitted to control the battery 50 to supply, or not supply, energy for the operation of the restriction device 4.

Figure 13:
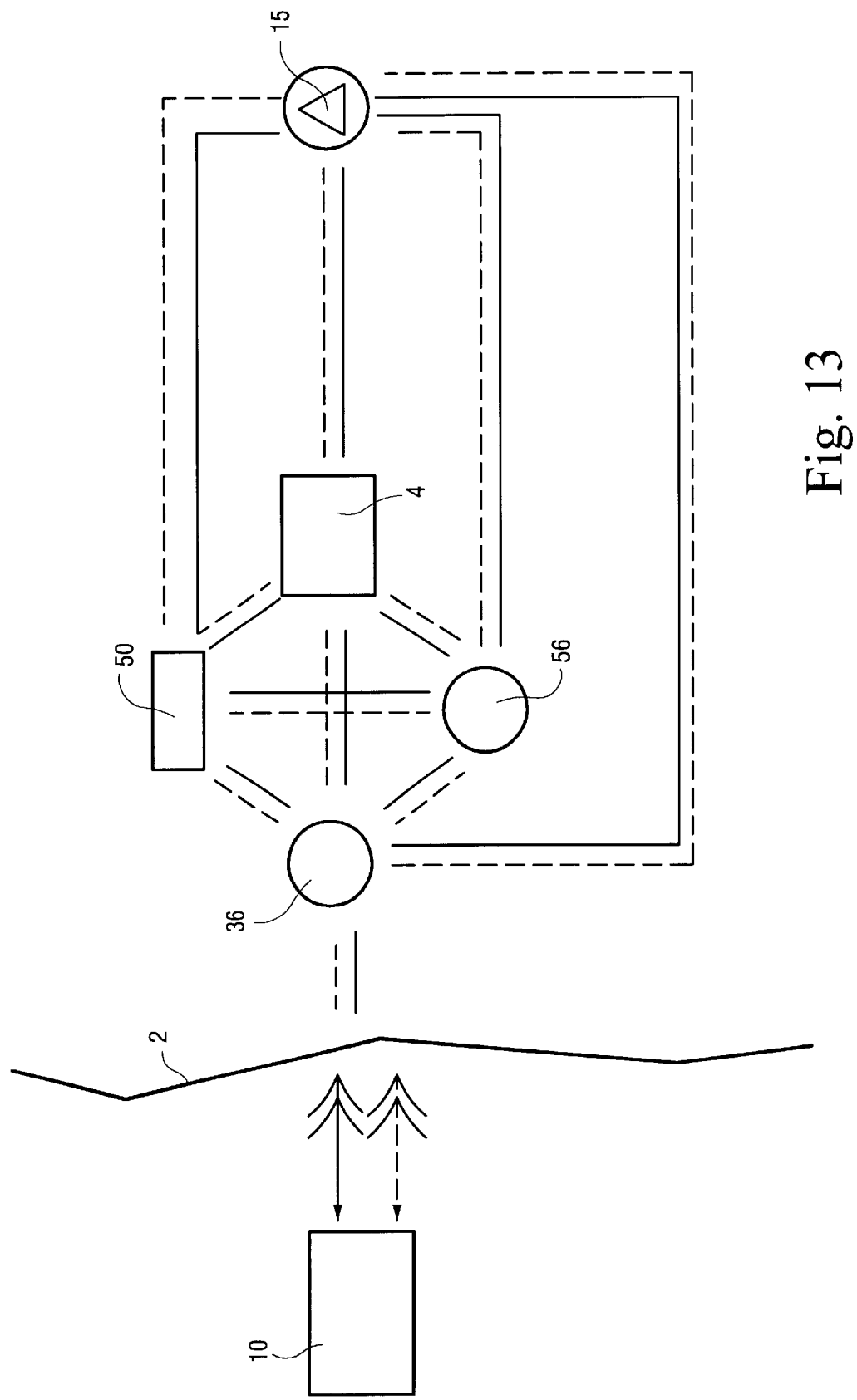
FIG. 13 is a schematic block diagram illustrating conceivable combinations of implanted components for achieving various communication options.

FIG. 13 schematically shows conceivable combinations of implanted components of the apparatus for achieving various communication options. Basically, there are the implanted restriction device 4, control unit 36 and motor/pump unit 18, and the external energy transmission device 10 including the external wireless remote control. As already described above the wireless remote control transmits a control signal which is received by the implanted control unit 36, which in turn controls the various implanted components of the apparatus.

A sensor 56 may be implanted in the patient for sensing a physical parameter of the patient, such as the pressure in the stomach. The implanted control unit 36, or alternatively the external wireless remote control of the energy transmission device 10, may control the restriction device 4 in response to signals from the sensor 56. A tranceiver may be combined with the sensor 56 for sending information on the sensed physical parameter to the external wireless remote control. The wireless remote control may comprise a signal transmitter or transceiver and the implanted control unit 36 may comprise a signal receiver or transceiver. Alternatively, the wireless remote control may comprise a signal receiver or transceiver and the implanted control unit 36 may comprise a signal transmitter or transceiver. The above transceivers, transmitters and receivers may be used for sending information or data related to the restriction device 4 from inside the patient's body to the outside thereof.

Where the motor/pump unit 18 and battery 50 for powering the motor/pump unit 18 are implanted, the battery 50 may be equipped with a tranceiver for sending information on the condition of the battery 50.

Those skilled in the art will realize that the above various embodiments according to FIGS. 1–13 could be combined in many different ways. For example, the energy operated switch 14 could be incorporated in any of the embodiments of FIGS. 3, 6–12, the hydraulic shifting device 34 could be incorporated in the embodiment of FIG. 4, and the gear box 54 could be incorporated in the embodiment of FIG. 3.

Figure 14:
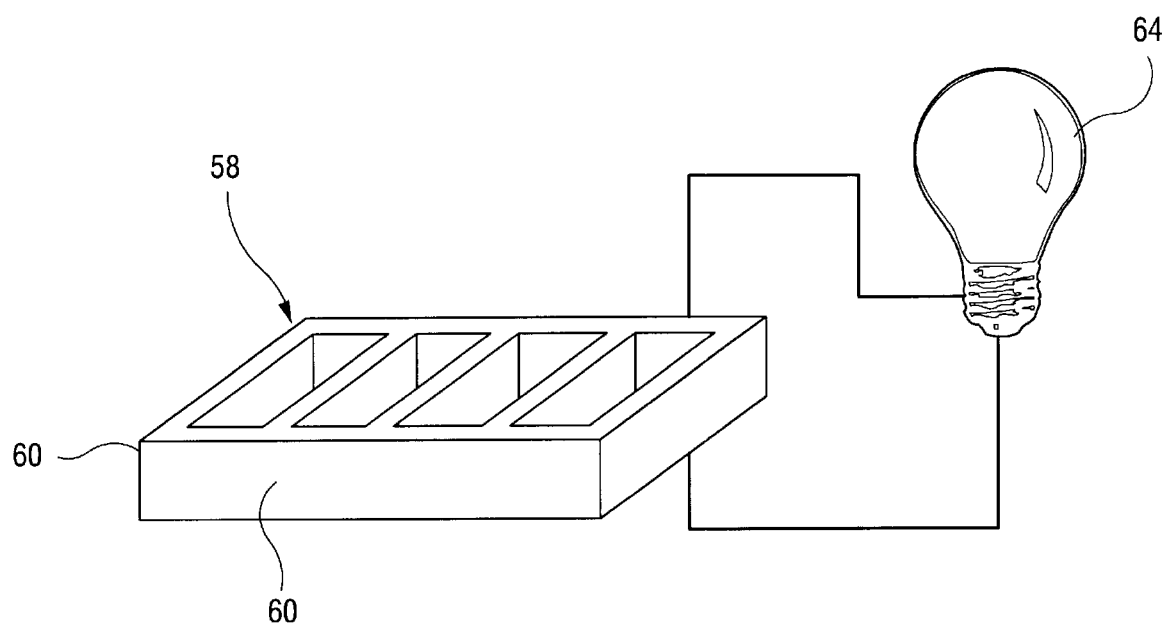
FIG. 14 illustrates an electrical junction element for use in the apparatus of the present invention.

FIG. 14 shows an energy transfer device in the form of an electrical junction element 58 for use in any of the above embodiments according to FIGS. 1–13. The element 58 is a flat p-n junction element comprising a p-type semiconductor layer 60 and an n-type semiconductor layer 62 sandwiched together. A light bulb 64 is electrically connected to opposite sides of the element 58 to illustrate how the generated current is obtained. The output of current from such a p-n junction element 58 is correlated to the temperature. See the formula below.

$$I = I0(\exp(qV/kT) - 1)$$

where

I is the external current flow,

I0 is the reverse saturation current, q is the fundamental electronic charge of $1.602 \times 10^{-19}$ coulombs, V is the applied voltage, k is the Boltzmann constant, and T is the absolute temperature.

Under large negative applied voltage (reverse bias), the exponential term becomes negligible compared to 1.0, and I is approximately –I0. I0 is strongly dependent on the temperature of the junction and hence on the intrinsic-carrier concentration. I0 is larger for materials with smaller bandgaps than for those with larger bandgaps. The rectifier action of the diode—that is, its restriction of current flow to only one direction—is in this particular embodiment the key to the operation of the p-n junction element 58.

An alternative way to design a p-n junction element is to deposit a thin layer of semiconductor onto a supporting material which does not absorb the kind of energy utilized in the respective embodiments. For use with wirelessly transmitted energy in terms of light waves, glass could be a suitable material. Various materials may be used in the semiconductor layers such as but not limited to cadmium telluride, copper-indium-diselenide and silicon. It is also possible to use a multilayer structure with several layers of p and n-type materials to improve efficiency.

The electric energy generated by the p-n junction element 58 could be of the same type as generated by solar cells, in which the negative and positive fields create a direct current. Alternatively, the negative and positive semiconductor layers may change polarity following the transmitted waves, thereby generating an alternating current.

The p-n junction element 58 is designed to make it suited for implantation. Thus, all the external surfaces of the element 58 in contact with the human body are made of a biocompatible material. The p-n junction semiconductors are designed to operate optimally at a body temperature of 37° C. because the current output, which should be more than 1 $\mu$A, is significantly depending on temperature as shown above. Since both the skin and subcutis absorb energy, the relation between the sensitivity or working area of the element 58 and the intensity or strength of the wireless energy transmission is considered. The p-n junction element 58 preferably is designed flat and small. Alternatively, if the element 58 is made in larger sizes it should be flexible, in order to adapt to the patient's body movements. The volume of the element 58 should be kept less than 2000 cm$^3$.

Figure 15:
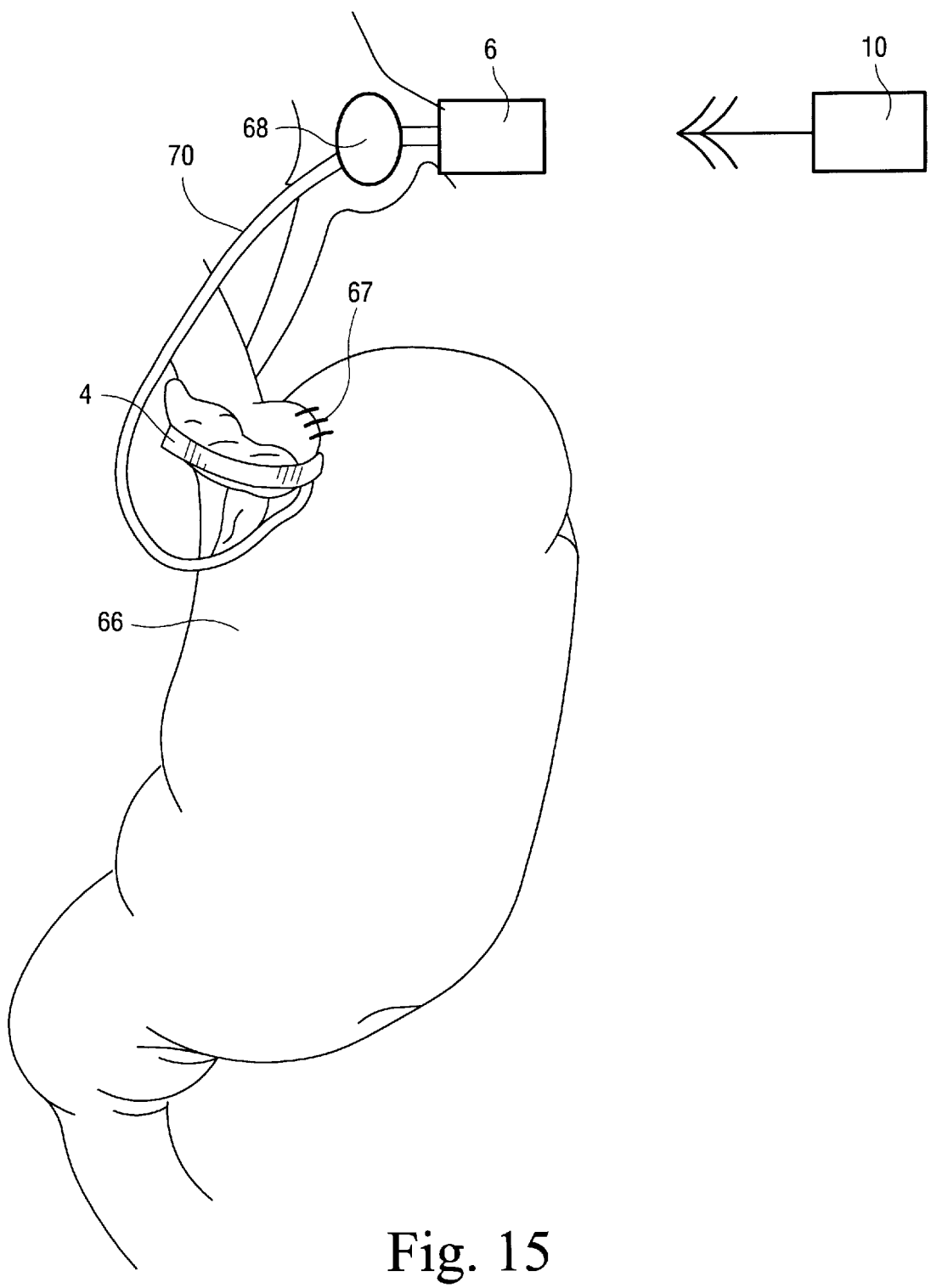
FIG. 15 illustrates the apparatus in accordance with the invention implanted in a patient.

FIG. 15 generally illustrates how any of the above-described embodiments of the food intake restriction apparatus of the invention may be implanted in a patient. Thus, a restriction device 4 implanted in a patient engages the stomach 66 to form a a small upper pouch 67 of the stomach and a restricted stoma opening in the stomach. An implanted operation device 68, which may also be referred to as an adjustment device, such as an electric motor or a motor/pump assembly, operates the restriction device 4 through a transmission member 70, such as a mechanical transmission cord or a fluid tube. An energy transfer device in the form of an element 6 having a positive region and a negative region, as described above in more detail, is placed underneath the skin of the patient.

Wireless energy carried by a signal transmitted by a wireless remote control of an external energy transmission device 10 at least partly penetrates the patient's skin and hits the element 6. The energy thus hitting the element 6 is transferred into energy of a different form that is suited for powering the operation device 68. For example, where the operation device 68 is an electric motor the element 6 comprises an electric p-n junction element that transfers the wireless energy into an electric current for powering the electric motor. Where the operation device 68 comprises a pump, the element 6 may transfer the wireless energy into kinetic energy for powering the pump.

The transferred energy may be utilized for directly operating the restriction device 4 or, where the restriction device 4 is electrically operated, for storage in a capacitor and/or an accumulator for later or parallel use. Preferably (but not necessarily) the element 6 is controlled by a microprocessor. The wireless remote control of the external energy transmission device 10 is used to control the utilization of the transmitted energy and any function or command to/from the implanted restriction device 4.

In the practice of the present invention the details of the elongated restriction device 4 (such as a gastric band) and the adjustment/operation device (which may have electric, hydraulic, or mechanical, etc. actuation) 6, may be as described in copending applications Ser. No. 09/133,319, filed Aug. 13, 1998 (Atty Ref: 2333-12), Ser. No. 09/133,320, filed Aug. 13, 1998 (Atty Ref: 2333-11) and Ser. No. 09/133,322, filed Aug. 13, 1998 (Atty Ref: 2333-13), the disclosures of which are incorporated by reference herein.

The invention also comprises or consists of the foregoing structures and method steps, and is to be interpreted as broadly as allowed by the prior art.

What is claimed is:

1. A food intake restriction apparatus for an obese patient, comprising:
    an energy transmission device for wireless transmission of energy of a first form from outside the patient's body;
    an operable restriction device adapted to be implanted in the patient to engage the stomach or the esophagus to form an upper small pouch of the stomach and a restricted stoma opening in the stomach or esophagus, said restriction device operable in response to a second energy form different than the first form energy to vary the restricted stoma; and
    an energy transfer device adapted to be implanted in the patient for transferring energy of the first form transmitted by said energy transmission device into energy of the second form,
        wherein said energy transfer device comprises at least one element having a positive region and a negative region, and creating an energy field between said positive and negative regions when exposed to the first form energy transmitted by said energy transmission device, so that said energy field produces the energy of the second form.

2. The apparatus according to claim 1, wherein said element comprises an electrical junction element capable of inducing an electric field between said positive and negative regions when exposed to the energy of the first form transmitted by said energy transmission device, whereby said energy of the second form comprises electric energy.

3. The apparatus according to claim 2, wherein said restriction device is electrically operated, and said positive and negative regions of said electrical junction element supply electric energy for the operation of said restriction device.

4. The apparatus according to claim 3, further comprising electric conductors connected to said positive and negative regions of said electrical junction element, whereby said electrical junction element is capable of supplying an electric current via said conductors.

5. The apparatus according to claim 4, wherein said electrical junction element is capable of supplying a direct current or pulsating direct current via said conductors.

6. The apparatus according to claim 3, wherein said electrical junction element is capable of supplying a frequency or amplitude modulated signal.

7. The apparatus according to claim 3, wherein said electrical junction element is capable of supplying an analog or digital signal.

8. The apparatus according to claim 4, wherein said electrical junction element is capable of supplying an alternating current or a combination of a direct and alternating current via said conductors.

9. The apparatus according to claim 2, wherein said electrical junction element comprises at least one semiconductor.

10. The apparatus according to claim 2, wherein said electrical junction element generates an output current exceeding 1 $\mu$A when exposed to the energy of the first form transmitted by said energy transmission device.

11. The apparatus according to claim 1, further comprising an operation device adapted to be implanted in the patient for operating said restriction device, wherein said element powers said operation device with the energy of the second form.

12. The apparatus according to claim 11, wherein said operation device comprise a motor.

13. The apparatus according to claim 12, further comprising a control device, wherein said motor comprises a rotary motor, and said control device controls said rotary motor to rotate a desired number of revolutions.

14. The apparatus according to claim 12, wherein said motor comprises a linear motor.

15. The apparatus according to claim 12, further comprising a control device, wherein said motor comprises a hydraulic or pneumatic fluid motor, and said control device controls said fluid motor.

16. The apparatus according to claim 12, wherein said motor comprises an electric motor having electrically conductive parts made of plastics.

17. The apparatus according to claim 11, wherein said restriction device comprises hydraulic means and said operation device comprises a pump for pumping a fluid in said hydraulic means.

18. The apparatus according to claim 17, wherein said operation device comprises a motor for driving said pump.

19. The apparatus according to claim 17, wherein said operation device comprises a fluid conduit between said pump and said hydraulic means of said restriction device, and a reservoir for fluid, said reservoir forming part of said conduit.

20. The apparatus according to claim 19, wherein said hydraulic means, pump and conduit are devoid of any non-return valve.

21. The apparatus according to claim 20, wherein said reservoir forms a fluid chamber with a variable volume, and said pump distributes fluid from said chamber to said hydraulic means of said restriction device by reduction of the volume of said chamber and withdraws fluid from said hydraulic means to said chamber by expansion of the volume of said chamber.

22. The apparatus according to claim 11, further comprising a control device for controlling said operation device.

23. The apparatus according to claim 22, wherein said control device shifts polarity of the energy of the second form to reverse said operation device.

24. The apparatus according to claim 23, wherein said operation device comprises an electric motor and the energy of the second form comprises electric energy.

25. The apparatus according to claim 22, wherein said restriction device is operable to perform a reversible function.

26. The apparatus according to claim 22, further comprising a reversing device adapted to be implanted in the patient for reversing said function performed by said restriction device.

27. The apparatus according to claim 26, wherein said control device controls said reversing device to reverse said function performed by said restriction device.

28. The apparatus according to claim 26, wherein said reversing device comprises hydraulic means including a valve for shifting the flow direction of a fluid flow in said hydraulic means.

29. The apparatus according to claim 26, wherein said reversing device comprises a mechanical reversing device.

30. The apparatus according to claim 29, wherein said reversing device comprises a gear box.

31. The apparatus according to claim 26, wherein said reversing device comprises a switch.

32. The apparatus according to claim 31, wherein said switch is operable by the energy of the second form.

33. The apparatus according to claim 32, wherein said control device controls the operation of said switch by shifting polarity of the energy of the second form.

34. The apparatus according to claim 32, wherein said switch comprises an electric switch and the energy of the second form comprises electric energy.

35. The apparatus according to claim 11, wherein said operation device comprises hydraulic means and at least one valve for controlling a fluid flow in said hydraulic means.

36. The apparatus according to claim 35, further comprising a wireless remote control for controlling said valve.

37. The apparatus according to claim 1, wherein said element forms a flat and thin sheet, and has a volume of less than 2000 cm$^3$.

38. The apparatus according to claim 1, further comprising an energy storage device adapted to be implanted in the patient for storing the energy of the second form and for supplying energy in connection with the operation of said restriction device.

39. The apparatus according to claim 38, wherein said energy storage device comprises an accumulator.

40. The apparatus according to claim 39, wherein the energy of the second form comprises electric energy and said energy storage device comprises an electric accumulator.

41. The apparatus according to claim 40, wherein said electric accumulator comprises at least one capacitor or at least one rechargeable battery, or a combination of at least one capacitor and at least one rechargeable battery.

42. The apparatus according to claim 38, further comprising a switch adapted to be implanted in the patient for directly or indirectly switching the operation of said restriction device.

43. The apparatus according to claim 42, further comprising a source of energy adapted to be implanted in the patient, wherein said switch is operated by the energy of the second form supplied by said energy storage device to switch from an off mode, in which said source of energy is not in use, to an on mode, in which said source of energy supplies energy for the operation of said restriction device.

44. The apparatus according to claim 42, further comprising a source of energy adapted to be implanted in the patient, and a remote control for controlling the supply of energy of said implantable source of energy, wherein said switch is operated by the energy of the second form supplied by said energy storage device to switch from an off mode, in which said remote control is prevented from controlling said source of energy and said source of energy is not in use, to a standby mode, in which said remote control is permitted to control said source of energy to supply energy for the operation of said restriction device.

45. The apparatus according to claim 1, further comprising a switch adapted to be implanted in the patient for switching the operation of said restriction device.

46. The apparatus according to claim 45, further comprising a source of energy adapted to be implanted in the patient for supplying energy for the operation of said restriction device, wherein said switch is operated by the energy of the second form supplied by said energy transfer device to switch from an off mode, in which said source of energy is not in use, to an on mode, in which said source of energy supplies energy for the operation of said restriction device.

47. The apparatus according to claim 45, further comprising a source of energy adapted to be implanted in the patient for supplying energy for the operation of said restriction device, and a remote control for controlling the supply of energy of said implanted source of energy, wherein said switch is operated by the energy of the second form supplied by said energy transfer device to switch from an off mode, in which said remote control is prevented from controlling said source of energy and said source of energy is not in use, to a standby mode, in which said remote control is permitted to control said source of energy to supply energy for the operation of said restriction device.

48. The apparatus according to claim 1, wherein said energy transmission device transmits the energy of the first form by at least one wireless signal.

49. The apparatus according to claim 48, wherein said signal comprises a wave signal.

50. The apparatus according to claim 49, wherein said wave signal comprises an electromagnetic wave signal including one of an infrared light signal, a visible light signal, an ultra violet light signal, a laser signal, a micro wave signal, a radio wave signal, an x-ray radiation signal, and a gamma radiation signal.

51. The apparatus according to claim 49, wherein said wave signal comprises a sound wave signal.

52. The apparatus according to claim 48, wherein said signal contains radiant energy.

53. The apparatus according to claim 48, wherein said signal comprises a digital or analog signal, or a combination of a digital and analog signal.

54. The apparatus according to claim 1, wherein the energy of the first form transmitted by said energy transmission device comprises an electric field.

55. The apparatus according to claim 54, wherein said electric field is transmitted in pulses or digital pulses by said energy transmission device.

56. The apparatus according to claim 1, wherein the energy of the first form transmitted by said energy transmission device comprises a magnetic field.

57. The apparatus according to claim 56, wherein said magnetic field is transmitted in pulses or digital pulses by said energy transmission device.

58. The apparatus according to claim 1, wherein said energy transfer device transfers the energy of the first form into a direct current or pulsating direct current, or a combination of a direct current and a pulsating direct current.

59. The apparatus according to claim 1, wherein said energy transfer device transfers the energy of the first form into an alternating current or a combination of a direct and alternating current.

60. The apparatus according to claim 1, wherein the energy of the second form comprises a frequency or amplitude modulated signal, or a combination of a frequency and amplitude modulated signal.

61. The apparatus according to claim 1, wherein the energy of the second form comprises an analog or a digital signal, or a combination of an analog and digital signal.

62. The apparatus according to claim 1, further comprising a pulse generator adapted to be implanted in the patient for generating electrical pulses from the energy of the second form rendered by said energy field.

63. The apparatus according to claim 1, further comprising at least one sensor adapted to be implanted in the patient for sensing at least one physical parameter of the patient.

64. The apparatus according to claim 63, wherein said sensor comprises a pressure sensor for directly or indirectly sensing the pressure against the stomach or esophagus or said restriction device.

65. The apparatus according to claim 63, further comprising a control device for controlling said restriction device in response to signals from said sensor.

66. The apparatus according to claim 65, wherein said control device comprises an internal control unit adapted to be implanted in the patient for controlling said restriction device in response to signals from said sensor.

67. The apparatus according to claim 65, wherein said internal control unit directly controls said restriction device in response to signals from said sensor.

68. The apparatus according to claim 65, wherein said control device comprises an external control unit outside the patient's body for controlling said restriction device in response to signals from said sensor.

69. The apparatus according to claim 68, wherein said external control unit stores information on said physical parameter sensed by said sensor and is manually operated to control said restriction device based on said stored information.

70. The apparatus according to claim 63, further comprising at least one sender adapted to be implanted in the patient for sending information on said physical parameter sensed by said sensor.

71. The apparatus according to claim 1, further comprising a wireless remote control transmitting at least one wireless control signal for controlling said restriction device.

72. The apparatus according to claim 71, wherein said remote control is capable of obtaining information on the condition of said restriction device and to control said restriction device in response to said information.

73. The apparatus according to claim 71, wherein said remote control comprises a control unit adapted to be implanted in the patient for controlling said restriction device.

74. The apparatus according to claim 73, wherein said control unit comprises a microprocessor.

75. The apparatus according to claim 71, wherein said wireless remote control comprises at least one external signal transmitter or transceiver and at least one internal signal receiver or transceiver adapted to be implanted in the patient.

76. The apparatus according to claim 71, wherein said wireless remote control comprises at least one external signal receiver or transceiver and at least one internal signal transmitter or transceiver adapted to be implanted in the patient.

77. The apparatus according to claim 71, wherein said remote control is capable of sending information related to said restriction device from inside the patient's body to the outside thereof.

78. The apparatus according to claim 77, wherein said remote control controls said restriction device in response to said information.

79. The apparatus according to claim 71, wherein said remote control comprises a control signal transmitter for transmitting said control signal, and said energy transmission device comprises said control signal transmitter, whereby the energy of the first form is transmitted by said control signal.

80. The apparatus according to claim 71, wherein said energy transmission device transmits the energy of the first form by at least one signal separate from said control signal.

81. The apparatus according to claim 71, wherein said remote control transmits a carrier signal for carrying said control signal.

82. The apparatus according to claim 71, wherein said energy transmission device transmits the energy of the first form by at least one signal, which is used as a carrier signal for said control signal transmitted by said remote control.

83. The apparatus according to claim 82, wherein said carrier signal is frequency or amplitude modulated, or frequency and amplitude modulated.

84. The apparatus according to claim 82, wherein said carrier signal comprises digital or analog waves, or a combination of digital and analog waves.

85. The apparatus according to claim 82, wherein said control signal used with said carrier signal is frequency or amplitude modulated, or frequency and amplitude modulated.

86. The apparatus according to claim 82, wherein said control signal used with said carrier signal is digital or analog, or digital and analog.

87. The apparatus according to claim 71, wherein said control signal comprises a wave signal comprising one of a sound wave signal including an ultrasound wave signal, an electromagnetic wave signal including an infrared light signal, a visible light signal, an ultra violet light signal and a laser light signal, a micro wave signal, a radio wave signal, an x-ray radiation signal, and a gamma radiation signal.

88. The apparatus according to claim 71, wherein said control signal comprises an electric or magnetic field, or an electric and magnetic field.

89. The apparatus according to claim 71, wherein said control signal comprises a digital or analog control signal, or a digital and analog control signal.

90. The apparatus according to claim 89, wherein said remote control transmits an electromagnetic carrier wave signal for carrying said digital or analog control signal.

91. The apparatus according to claim 1, wherein the energy of the second form used for operating said restriction device is wirelessly transmitted by said energy transfer device.

92. The apparatus according to claim 1, wherein said restriction device controls the size of the stoma opening.

93. The apparatus according to claim 1, further comprising a control unit adapted to be implanted in the patient for controlling said restriction device.

94. The apparatus according to claim 93, wherein said control unit is programmable for controlling said restriction device in accordance with a program.

95. The apparatus according to claim 94, wherein said control unit controls said restriction device over time in accordance with an activity schedule program.

96. The apparatus according to claim 94, further comprising an external wireless remote control for programming said control unit.

97. The apparatus according to claim 1, further comprising an external data communicator and a data communicator adapted to be implanted in the patient communicating with said external communicator, wherein said implantable data communicator feeds data related to said restriction device back to said external communicator or said external communicator feeds data to said implantable data communicator.

98. The apparatus according to claim 97, wherein said implantable data communicator feeds data related to at least one physical signal of the patient.

99. The apparatus according to claim 1, wherein said restriction device is non-inflatable.

100. The apparatus according to claim 1, wherein said restriction device is directly operated with the energy of the second form, as said energy transmission device transmits the energy of the first form.

101. The apparatus according to claim 100, wherein said restriction device is directly operated with the energy of the second form in a non-magnetic manner.

102. The apparatus according to claim 100, wherein said restriction device is adapted for direct operation with the energy of the second form, when said restriction device is implanted in the patient, without externally touching components of the apparatus that are adapted to be subcutaneously implanted in the patient.

103. The apparatus according to claim 1, wherein the energy of the first form comprises kinetic energy.

104. The apparatus according to claim 1, wherein said energy transfer device is adapted to be implanted subcutaneously or in the abdomen of the patient.

105. The apparatus according to claim 1, wherein said energy transfer device is adapted to be implanted in the thorax or in the cephalic region of the patient.

106. The apparatus according to claim 1, wherein said energy transfer device is adapted to be implanted in an orifice of the patient's body and under the mucosa or intraluminar outside the mucosa of the orifice.

107. A food intake restriction apparatus for an obese patient, comprising:
   an energy transmission device for wireless transmission of energy of a first form from outside the patient's body;
   an operable restriction device adapted to be implanted in the patient to engage the stomach or the esophagus to form an upper small pouch of the stomach and a restricted stoma opening in the stomach or esophagus, said restriction device operable in response to a second energy form different than the first form energy to vary the restricted stoma; and
   an energy transfer device adapted to be implanted in the patient for transferring energy of the first form transmitted by said energy transmission device into energy of the second form,
      wherein said energy transfer device comprises at least one semiconductor circuitry creating an energy field when exposed to the first form energy transmitted by said energy transmission device, and said energy field provides the second form energy.

108. A food intake restriction apparatus for an obese patient, comprising:
   an energy transmission device for wireless transmission of energy of a first form from outside the patient's body;
   an operable restriction device adapted to be implanted in the patient to engage the stomach or the esophagus to form an upper small pouch of the stomach and a restricted stoma opening in the stomach or esophagus, said restriction device operable in response to a second energy form different than the first form energy to vary the restricted stoma; and
   an energy transfer device adapted to be implanted in the patient for transferring energy of the first form transmitted by said energy transmission device into energy of the second form,
      wherein said energy transfer device comprises at least one transistor circuitry creating an energy field when exposed to the first form energy transmitted by said energy transmission device, and said energy field provides the second form energy.

109. A food intake restriction apparatus for an obese patient, comprising:
   an energy transmission device for wireless transmission of energy of a first form from outside the patient's body;
   an operable restriction device adapted to be implanted in the patient to engage the stomach or the esophagus to form an upper small pouch of the stomach and a restricted stoma opening in the stomach or esophagus, said restriction device operable in response to a second energy form different than the first form energy to vary the restricted stoma; and
   an energy transfer device adapted to be implanted in the patient for transferring energy of the first form transmitted by said energy transmission device into energy of the second form;
      wherein said energy transfer device comprises at least one microchip creating an energy field when exposed to the first form energy transmitted by said energy transmission device, and said energy field provides the second form energy.

110. An implanting method, comprising the steps of providing a food intake restriction apparatus according to claim 1, cutting an opening in a patient's mucosa in an orifice of the patient's body, and implanting the energy transfer device in the patient's body through the opening.

111. An implanting method, comprising the steps of providing a food intake restriction apparatus according to claim 1, cutting an opening in a patient's skin, and implanting the energy transfer device in the patient's body through the opening.

112. A laparascopical implanting method, comprising the steps of providing a food intake restriction apparatus according to claim 1, placing at least two laparascopic cannula within a patient's body, and implanting the energy transfer device in the patient's body by using the at least two laparascopic cannula.

113. A laparoscopic surgical method of implanting in a patient a food intake restriction apparatus, comprising the steps of:
   a) placing at least two laparoscopic cannula within the patient's body,
   b) using a dissecting tool inserted through the laparoscopic trocar, dissecting the region of the esophagus or stomach,
   c) introducing the restriction device through the trocar,
   d) placing a restriction device of the apparatus in engagement with the esophagus or the upper part of the stomach to create an upper pouch of the stomach and a restricted stoma opening,
   e) implanting in the patient an energy transfer device of the apparatus including at least one element having a positive region and a negative region, and creating an energy field between the positive and negative regions when exposed to wireless energy of a first form,
   f) exposing the at least one element to the first form energy so that the energy field created between the positive and negative regions produces energy of a second form different than the first form energy, and g) operating the restriction device with the second form energy produced by the energy transfer device to vary the restricted stoma opening.

114. A method as recited in claim 113 further comprising post-operatively adjusting the restricted stoma in a non-invasive procedure.

* * * * *